United States Patent
Pack et al.

(10) Patent No.: US 10,082,473 B2
(45) Date of Patent: Sep. 25, 2018

(54) X-RAY FILTRATION

(71) Applicant: GENERAL ELECTRIC COMPANY, Schenectady, NY (US)

(72) Inventors: Jed Douglas Pack, Glenville, NY (US); Vance Scott Robinson, Schenectady, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 49 days.

(21) Appl. No.: 14/793,432

(22) Filed: Jul. 7, 2015

(65) Prior Publication Data

US 2017/0011815 A1 Jan. 12, 2017

(51) Int. Cl.
*G21K 3/00* (2006.01)
*G01N 23/046* (2018.01)
*G21K 1/02* (2006.01)

(52) U.S. Cl.
CPC ........... *G01N 23/046* (2013.01); *G21K 1/025* (2013.01); *G01N 2223/313* (2013.01); *G01N 2223/419* (2013.01)

(58) Field of Classification Search
CPC ........... A61B 6/032; A61B 6/06; A61B 6/542; A61B 6/4021; A61B 6/4291; A61B 6/4085; A61B 6/488; A61B 6/583; A61B 6/027; A61B 6/037; A61B 6/4233; A61B 6/5205; A61B 6/4028; A61B 6/4258; A61B 6/544; A61B 6/00; A61B 6/035; A61B 6/04; A61B 6/4035; A61B 6/0457; A61B 6/0492; A61B 6/08; A61B 6/40; A61B 6/502; G21K 1/10; G21K 1/043; G21K 1/046; G21K 1/02; G21K 5/10; A61L 2202/23; A61L 2/082; A61L 2/087; B67C 2003/228; B67C 2003/2688; B67C 3/22; B67C 3/242; B67C 7/0053; B67C 7/0073; B82Y 10/00;
(Continued)

(56) References Cited

U.S. PATENT DOCUMENTS 2,688,095 A * 8/1954 Andrews .............. G01N 23/205
250/208.4
3,780,291 A 12/1973 Stein
(Continued)

FOREIGN PATENT DOCUMENTS

EP 0074021 A1 3/1983
EP 1772874 A3 4/2007

OTHER PUBLICATIONS

Sperl et al., "Optimized Intensity Modulation for Dose/Noise Reduction in X-ray Computed Tomography",Thesis, Technical University of Munich Centre for Mathematical Sciences, pp. 1-116, 2010.
(Continued)

*Primary Examiner* — Irakli Kiknadze
(74) *Attorney, Agent, or Firm* — GE Global Patent Operation; Pabitra Chakrabarti

(57) ABSTRACT

An X-ray filter assembly is disclosed having a stack of X-ray attenuating sheets that are angled so as to have a focus point. When implemented in an imaging system, the focus point of the filter assembly is spatially offset (e.g., behind) the X-ray emission location. The filter assembly may be used (e.g., translated, rotated, and so forth) to adjust the intensity profile of the X-rays seen in an imaging volume.

17 Claims, 11 Drawing Sheets

(58) Field of Classification Search
CPC .. B82Y 20/00; B82Y 5/00; G01N 2021/6439; G01N 33/56966; G01N 15/1429; G01N 15/1475
USPC .............. 378/4, 19, 119, 145, 147–160
See application file for complete search history.

(56) References Cited

U.S. PATENT DOCUMENTS

| | | | |
|---|---|---|---|
| 4,277,684 A | | 7/1981 | Carson |
| 4,672,648 A | * | 6/1987 | Mattson ............... G21K 1/025 378/149 |
| 4,741,012 A | * | 4/1988 | Duinker ................ A61B 6/06 378/145 |
| 5,038,370 A | | 8/1991 | Harding et al. |
| 6,272,206 B1 | | 8/2001 | Bjorkholm |
| 6,370,228 B1 | | 4/2002 | Mockler et al. |
| 6,426,999 B2 | | 7/2002 | Prins |
| 6,778,636 B1 | | 8/2004 | Andrews |
| 7,209,547 B2 | | 4/2007 | Baier et al. |
| 7,315,611 B2 | * | 1/2008 | Cho .................... A61B 6/032 378/156 |
| 7,769,127 B2 | | 8/2010 | Hoffman |
| 7,812,329 B2 | * | 10/2010 | Bykanov ........... G03F 7/70033 250/492.2 |
| 7,983,385 B2 | | 7/2011 | Heuscher et al. |
| 7,983,391 B2 | | 7/2011 | Machan et al. |
| RE43,036 E | * | 12/2011 | Sjmaenok ............. B82Y 10/00 378/156 |
| 8,094,785 B2 | | 1/2012 | Heid |
| 8,311,184 B2 | * | 11/2012 | Lee ...................... A61B 6/032 378/16 |
| 9,204,852 B2 | | 12/2015 | Edic et al. |
| 2004/0081273 A1 | | 4/2004 | Ning |
| 2004/0131158 A1 | * | 7/2004 | Hoheisel ................ G21K 1/10 378/154 |
| 2007/0110210 A1 | | 5/2007 | Nishide et al. |
| 2011/0075805 A1 | | 3/2011 | MacHan et al. |
| 2012/0140874 A1 | | 6/2012 | Li et al. |

OTHER PUBLICATIONS

Hess et al., "Optimizing image quality and dose in digital radiography of pediatric extremities", Philips, pp. 1-8, 2011.
Zoltowski, "Techniques to lower CT dose", GE Healthcare, pp. 1-3, Jun. 2011.
Katsuda et al., "Using Compensating Filters to Reduce Radiation Dose", Radiologic Technology, vol. No. 68, Issue No. 1, pp. 18-22, Sep.-Oct. 1996.
Yu et al., "Radiation Dose Reduction in Computed Tomography: Techniques and Future Perspective", Imaging in Medicine, vol. No. 1, Issue No. 1, pp. 65-84, Oct. 2009.

* cited by examiner

X-RAY FILTRATION

BACKGROUND

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation passes through a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a patient's body. In CT systems a detector array, including a series of detector elements, produces similar signals through various positions as a gantry is displaced around a patient.

In practice, a physician may only be interested in examining a limited portion of the patient's anatomy for the purpose of formulating a diagnosis. In such a circumstance, it may be desirable to minimize or reduce the X-ray exposure of the patient while still providing sufficient information to produce an accurate diagnosis. That is, it is generally desirable to reduce or minimize X-ray exposure of those portions of the patient anatomy not presently of interest, while still obtaining quality images of the anatomic region-of-interest. In many contexts, this may be difficult to effectively achieve as the region-of-interest will often be located at a different fan angle range with respect to the X-ray beam as a function of the view angle as the X-ray source is rotated about the patient.

Conventional approaches to address this issue may involve the use of a bowtie filter or collimator to adapt the intensity of the X-ray beam, such as in response to the apparent patient thickness in the imaging area at a given viewing angle. However, in practice it may be difficult to move a bowtie filter or collimator quickly back and forth in a manner that provides suitable results.

BRIEF DESCRIPTION

In accordance with a first embodiment, an X-ray filter assembly is provided. The X-ray filter assembly includes a plurality of X-ray attenuating sheets arranged in a stack. The X-ray attenuating sheets are angled with respect to one another so as to have a focus point that is converged upon by transmission pathways between the X-ray attenuating sheets.

In accordance with a second embodiment, an X-ray imaging system is provided. The X-ray imaging system includes an X-ray detector configured to generate signals in response to incident X-ray radiation, an X-ray source configured to emit X-rays from an X-ray emission point and through an imaging volume toward the X-ray detector, and a data acquisition system configured to readout signals from the X-ray detector. The X-ray imaging system further includes at least one X-ray filter positioned between the X-ray source and the imaging volume. The X-ray filter or filters have a focus that is spatially offset from the X-ray emission point.

In accordance with a third embodiment, a method for filtering X-rays is provided. In accordance with this method, X-rays are generated at an X-ray emission point of an X-ray source. At least a portion of the X-rays are filtered through an X-ray filter assembly positioned between the X-ray source and an imaging volume. The X-ray filter assembly has a focus spot spatially offset from the X-ray emission point. X-rays are detected at a detector positioned opposite the X-ray source and X-ray filter assembly across the imaging volume.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with systemrelated and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

The present X-ray filtration approaches employ a source-side filter assembly (i.e., the assembly is positioned between the X-ray source and the patient, rather than between the patient and the detector) that can be used to control the X-ray beam intensity profile using only small or limited motions of either the filter assembly or the X-ray emission focal spot, In certain embodiments, the X-ray filter assembly consists of a series of laminae that are, typically, focused at a location other than the X-ray focal spot (i.e., the source spot from which X-rays are generated). By way of example, the laminae may be focused on a point behind the X-ray focal spot (i.e., further away) with respect to the overall imaging context. Small or limited motions of the filter assembly or of the focal spot result in changes to the X-ray intensity profile seen at the patient and can be used to limit X-ray exposure at those regions not of interest in the patient. The mechanical motion required in these approaches is small (or zero in the case of a steered focal spot motion implementation).

Figure 1:
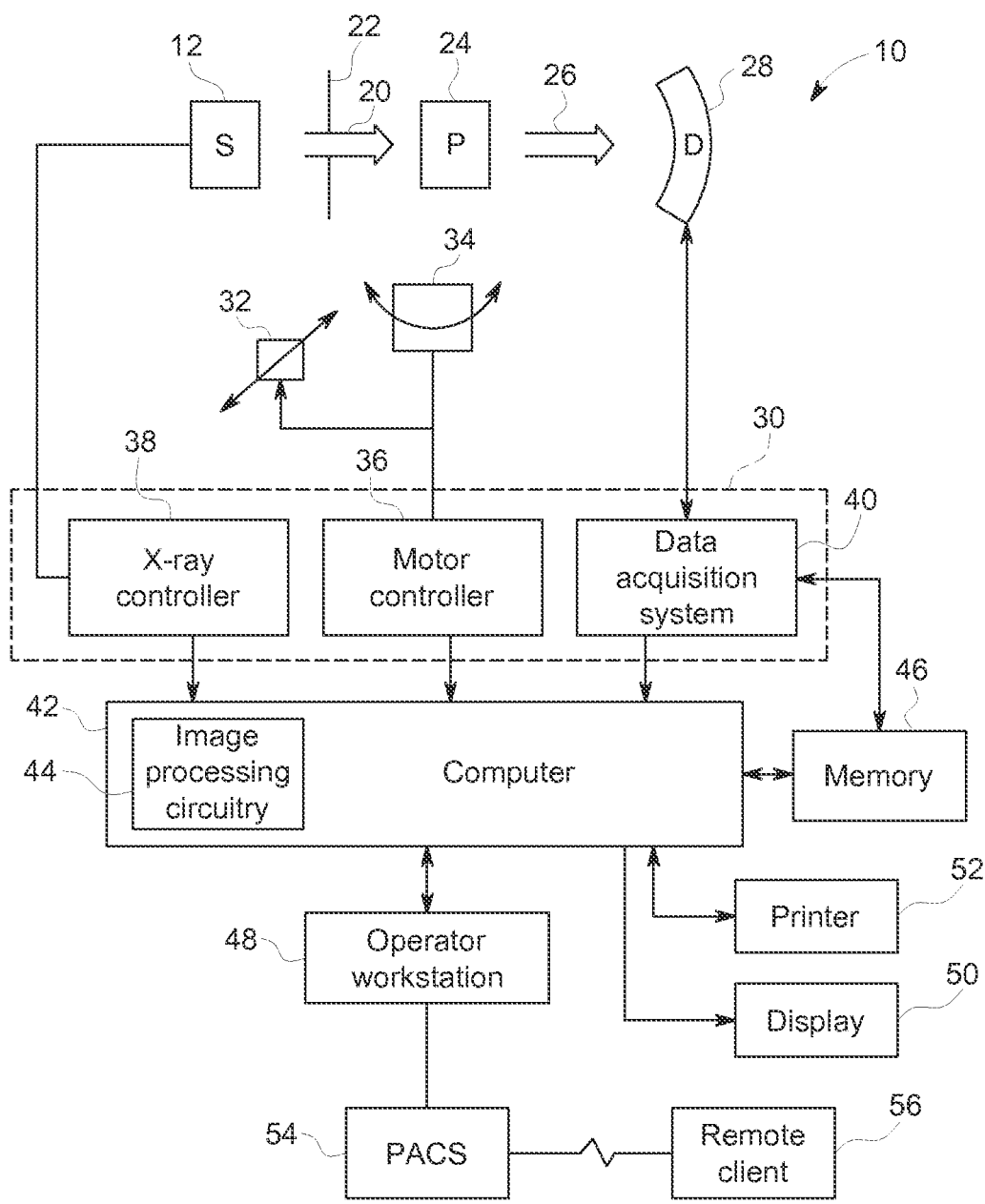
FIG. 1 is a schematic illustration of an embodiment of a computed tomography (CT) system configured to acquire CT images of a patient and to process the images in accordance with aspects of the present disclosure.

With the foregoing discussion in mind, FIG. 1 illustrates an embodiment of an imaging system 10 for acquiring and processing image data in accordance with aspects of the present disclosure. In the illustrated embodiment, system 10 is a computed tomography (CT) system designed to acquire X-ray projection data, to reconstruct the projection data into a tomographic image, and to process the image data for display and analysis. The CT imaging system 10 includes an X-ray source 12. As discussed in detail herein, the source 12 may include one or more X-ray sources, such as an X-ray tube or solid state emission structures. The X-ray source 12, in accordance with certain contemplated embodiments, is configured to emit an X-ray beam 20 from one or more emission spots (e.g., focal spots), which may correspond to X-ray emission regions on a target structure (e.g., an anode structure) impacted by a directed electron beam.

In certain implementations, the source 12 may be positioned proximate to a filter assembly 22, as discussed herein, that may be used to define an intensity profile of the X-ray beam 22 at a given time. For example, as discussed herein, the filter assembly 22 may be used to steer the X-ray beam 20, to define the shape or size of a high-intensity region of the X-ray beam 20, and/or to otherwise limit incidence of the X-rays on those portions of the patient 24 not within a region-of-interest. In practice, the filter assembly 22 may be incorporated within the gantry between the source 12 and the imaged volume.

The X-ray beam 20, after transmission through the filter assembly 22, passes into a region in which the subject (e.g., a patient 24) or object of interest is positioned. The patient 24 attenuates at least a portion of the X-rays 20, resulting in attenuated X-rays 26 that impact a detector array 28 formed by a plurality of detector elements (e.g., pixels). Each detector element produces an electrical signal that represents the intensity of the X-ray beam incident at the position of the detector element when the beam strikes the detector 28. Electrical signals are acquired and processed to generate one or more scan datasets.

A system controller 30 commands operation of the imaging system 10 to execute filtration, examination and/or calibration protocols and to process the acquired data. With respect to the X-ray source 12, the system controller 30 furnishes power, focal spot location, control signals and so forth, for the X-ray examination sequences. In accordance with certain embodiments, the system controller 30 (either via the X-ray controller 38 and/or motor controller 36 discussed below) may also control operation (e.g., linear or rotational translation) of the filter assembly 22 over the course of an examination.

The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, and to process the data acquired by the detector 28 in accordance with the steps and processes discussed herein. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal spot locations to the source 12. In addition, in some embodiments the X-ray controller 38 may be configured to selectively activate the source 12 such that tubes or emitters at different locations within the system 10 may be operated in synchrony with one another or independent of one another.

The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer 42 may include or communicate with one or more non-transitory memory devices 46 that can store data processed by the computer 42, data to be processed by the computer 42, or instructions to be executed by a processor 44 of the computer 42. For example, a processor of the computer 42 may execute one or more sets of instructions stored on the memory 46, which may be a memory of the computer 42, a memory of the processor, firmware, or a similar instantiation.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Keeping in mind the operation of the system 10 and, specifically, the X-ray source 12 discussed above with respect to FIG. 1, examples of the operation and construction of the filter assembly 22 are now described. It should be appreciated that the present approaches may have application in various X-ray imaging contexts, including conventional X-ray radiography, in addition to the presently described CT implementations. In certain embodiments, the filter assembly 22 is formed as a stack of laminae, each of which is a sheet of a material that attenuates X-rays (e.g., a metal such as tungsten, molybdenum, iron, nickel, copper, zinc, silver, tin, tantalum, gold, lead, rhenium, or other high atomic number materials). X-rays that pass through the filter assembly 22 without impacting these sheets (e.g., travel substantially parallel to the sheets) are less likely to be absorbed by the filtration than X-rays that pass through in an orientation for which the X-ray photons will impact one or more of the sheets (e.g., that pass at an angle relative to the sheets). In certain implementations, the focus point of these sheets is offset from (i.e., not collocated with) the emission point of the X-ray beam (i.e., the focal spot on the X-ray emitting target structure). The position and/or orientation of the filter assembly can thereby control which fan angles are transmitted efficiently and which are not.

By way of example, and as discussed in greater detail below, in certain implementations, if the filter assembly 22 is translated slightly in the x-dimension (i.e., the fan angle direction) relative to the X-ray emission focal spot, a high-intensity transmitted portion of the X-ray beam 20 is scanned in the fan angle direction of the system 10. If this is done in a generally sinusoidal pattern, and in synchrony with the rotation 12 about the patient 24, the result is that the high-intensity portion of the beam 20 remains directed at substantially the same region (e.g., the region-of-interest) within the patient 24. Alternatively, in other implementations the filter assembly 22 can be rotated relative to the X-ray emission focal spot instead of translated. A further option for beam steering is that the focal spot of the X-ray source can be moved (i.e., steered) instead of moving the filter assembly. Such an approach requires no mechanical motion of the filter assembly as the focal spot can be manipulated using the electromagnetic optics associated with the source 12. Beam steering can be achieved in this manner since the position and/or orientation of the filter assembly 22 relative to the focal spot is the determinative factor.

Further, relative motion of the filter assembly 22 (or of the focal spot) in the y-dimension (i.e., the direction of propagation of the X-rays at fan angle zero) can control the size (e.g., width) of the high-intensity portion of the beam 20, thereby allowing the operator to have high image quality in a larger (or smaller) region-of-interest. Also, the focal length can be adjusted as a function of z position (the scanner axis direction) either by stacking a discrete number of filter assemblies 22 or making the attenuating sheets twist in the z-dimension, such that motion in z (rather than y) can be used to control the aperture of the high-intensity portion of the beam 20. In addition, it should be appreciated that the present approach can be applied in another direction (e.g., the cone angle direction). For example, two such filter assemblies 22 could be used to perform 2D steering of a high intensity portion of the conical beam.

In one embodiment, an operator could specify a 1D or 2D region that requires high image quality, and the focal spot could be scanned (or the filter assemblies 22 translated) over time while the mA is (optionally) dynamically adjusted. A series of image frames can be digitally captured over this time and combined into a single image in which the image quality is highest in the region-of-interest, while the dose is reduced to other parts of the anatomy, where image quality (e.g., noise level) is less important to the diagnosis.

With the preceding in mind, certain examples of the fabrication and structure of filtration assemblies 22 are discussed herein, in accordance with certain implementations. For example, in one such implementation, the filter assembly 22 may be formed as a stack of separated sheets or layers of X-ray attenuating material (such as a molybdenum foil). In such an embodiment, the X-ray attenuating sheets may be spaced apart so that some paths exist through the stack for an X-ray photon to pass through unimpeded, while other paths result in one or more sheets of X-ray attenuating material being impacted.

Figure 2:
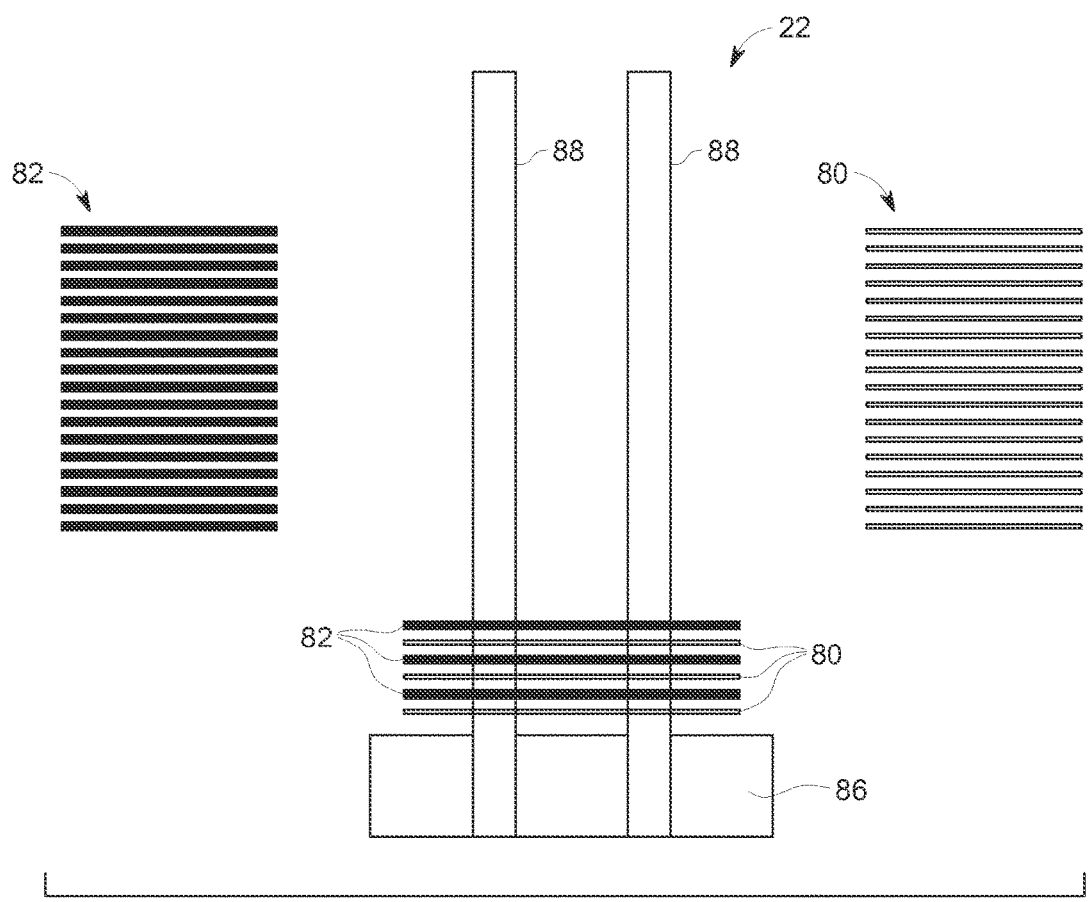
FIG. 2 depicts an X-ray filter assembly in the process of fabrication, in accordance with aspects of the present disclosure.

By way of example, and turning to FIG. 2, one embodiment of a filter assembly 22 may be fabricated by stacking in alternation sheets 80 of X-ray attenuating material (e.g., molybdenum) and sheets 82 of X-ray transmissive (i.e., non-attenuating) material (e.g., polyimide, such as Kapton®, or other materials having a low mass density and/or primarily composed of low atomic number elements, such as hydrogen, nitrogen, carbon, or oxygen). Stacking of the sheets 80, 82, may be facilitated by use of one or more end-blocks or plates 86 (e.g., an aluminum block) and one or more alignment rods 88 or other similar alignment and spacing feature. For example, each sheet 80, 82 may contain aligned through-holes (or other external or internal alignment features) that allow the sheet to be threaded onto the alignment rods 88 to form the stack of sheets. The alignment rods 88 may be secured to or threaded through an end-block or plate 86 and, once the stack of sheets 80, 82 is assembled, a corresponding end-block or plate 86 may be secured opposite the first end-block 86 to secure the stack.

By way of example, the attenuating sheets 80 may be formed from 0.1 to 5 mil (e.g. 1 mil) thick molybdenum foil which has been cut (e.g., laser cut) to the appropriate size and to include guide holes for the alignment rods 88 or other alignment features. In such an embodiment, the transmissive sheets 82 may be formed from 1 to 50 mil (e.g., 10 mil) thick polyimide film which has also been cut (e.g., laser cut) to the appropriate size and to include guide holes or other alignment features. Depending on the embodiment, a stack may consist of 200 to 1,000 pairs of attenuating and transmissive sheets 80, 82 (i.e., 400 to 2,000 total sheets), or may include numbers of sheets outside this range as warranted by the application. In one example, approximately 365 attenuating sheets 80 and a corresponding number of transmissive sheets 82 are stacked in an alternating arrangement to form a stack that is approximately 4 inches in height (assuming 1 mil thick attenuating sheets 80 and ~10 mil thick transmissive sheets 82) and which forms the basis for an embodiment of the filter assembly 22. As will be appreciated, other mechanisms or geometries for aligning and holding X-ray attenuating sheets 80 may also be employed, such as using a slotted holder assembly, or externally provided rails or alignment features. Thus, description or discussion of particular fabrication approaches herein should be understood to be provided as examples only and merely provided to facilitate explanation of the present approaches.

In certain implementations, the transmissive sheets 82 may be tapered or otherwise vary in thickness across all or part of their length, resulting in the stacked attenuating sheets 80 being angled (i.e., not parallel) to one another when stacked. As discussed below, such a tapering of the transmissive sheets 82 may be employed to determine a focus of the filter assembly 22 when the stack of transmissive and attenuating sheets 82, 80 is assembled. In particular, the X-ray attenuating sheets 80 may be angled slightly with respect to one another (such as due to the use of tapered transmissive sheets 80 in the stack) so as to establish a "focus point" determined or defined by the convergence of the respective pathways through the adjacent attenuating sheets 80 (where the pathways generally correspond to the locations of the transmissive sheets 82 separating the attenuating sheets 80). That is, the focus point defined for a given filter assembly 22 corresponds to the convergence point of the transmission paths between the attenuating sheets 80.

Figure 3:
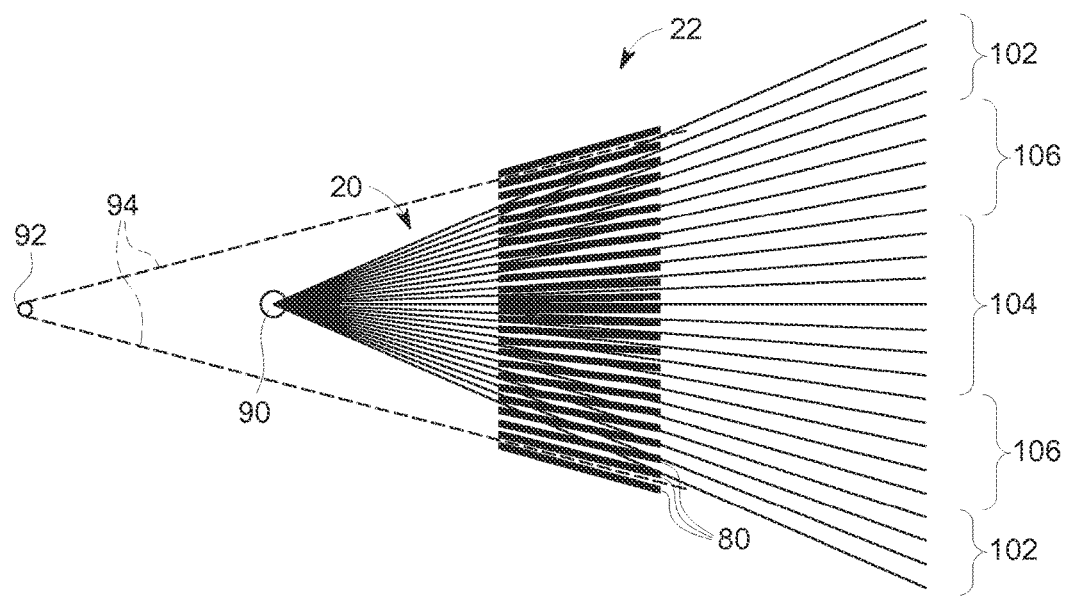
FIG. 3 depicts the effects of an embodiment of a filter assembly on X-ray transmission, in accordance with aspects of the present disclosure.

This is shown diagrammatically in FIG. 3, where a stack of attenuating sheets 80 of a filter assembly 22 is shown in conjunction with an X-ray emission point 90 (i.e., an X-ray focal spot) of an X-ray source 12. In the depicted example, the focus point 92 of the filter assembly 22 is depicted as the junction of dotted lines 94 corresponding to the transmission paths through the filter assembly 22. In accordance with certain present implementations, the focus point 92 does not correspond to the spatial location of the X-ray emission point 90, but instead is focused at a different position, such as behind the emission point 90 relative to the assembly 22, as depicted in the present example.

Because the focus of the filter assembly 22 is not on the X-ray emission point 90, the filter assembly 22 differentially attenuates and shapes the intensity profile of the emitted X-rays. By way of example, and as shown in FIG. 3, X-rays measured at locations 102 relative to the filter assembly 22 will have passed through at least two attenuating sheets 80 (e.g., two, three, or more attenuating sheets 80) on average. As a result, the observed X-ray intensity in these regions 102 will be reduced on average or in the aggregate. Conversely, X-rays measured at locations 104 relative to the filter assembly 22 will have passed through no more than one, and often zero, attenuating sheets 80 on average. As a result, the observed X-ray intensity in this region 104 will be at full or high-intensity, with little or no attenuation. X-rays measured at locations 106 relative to the filter assembly 22 will have passed through at least one attenuating sheet 80 (e.g., one or two attenuating sheets 80). As a result, the observed X-ray intensity in these regions 106 will be reduced on average or in the aggregate, but less so than what is observed in the regions 102, where greater attenuation is observed.

Figure 4:
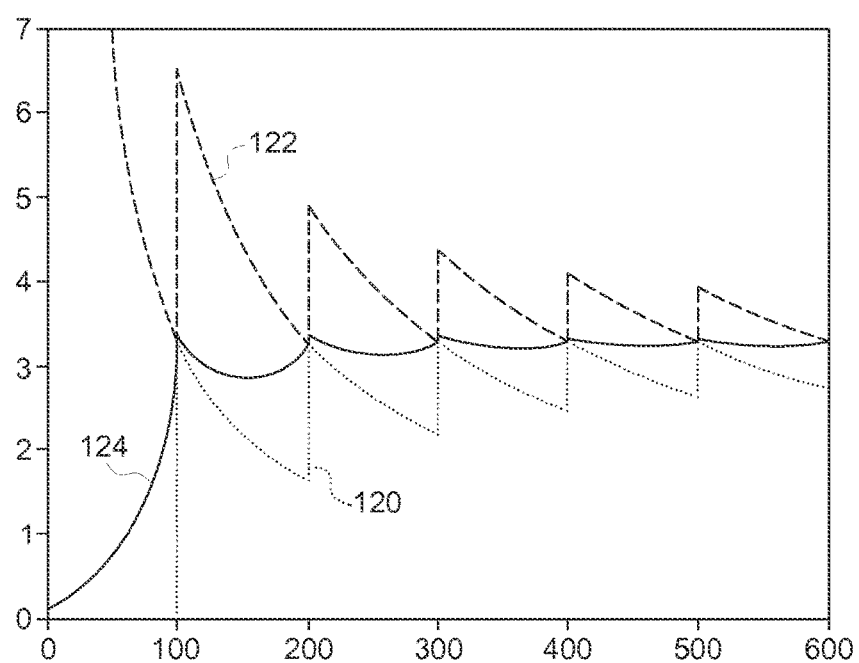
FIG. 4 graphically depicts simulated X-ray attenuation attributable to an X-ray filter assembly in accordance with aspects of the present disclosure.
Figure 5:
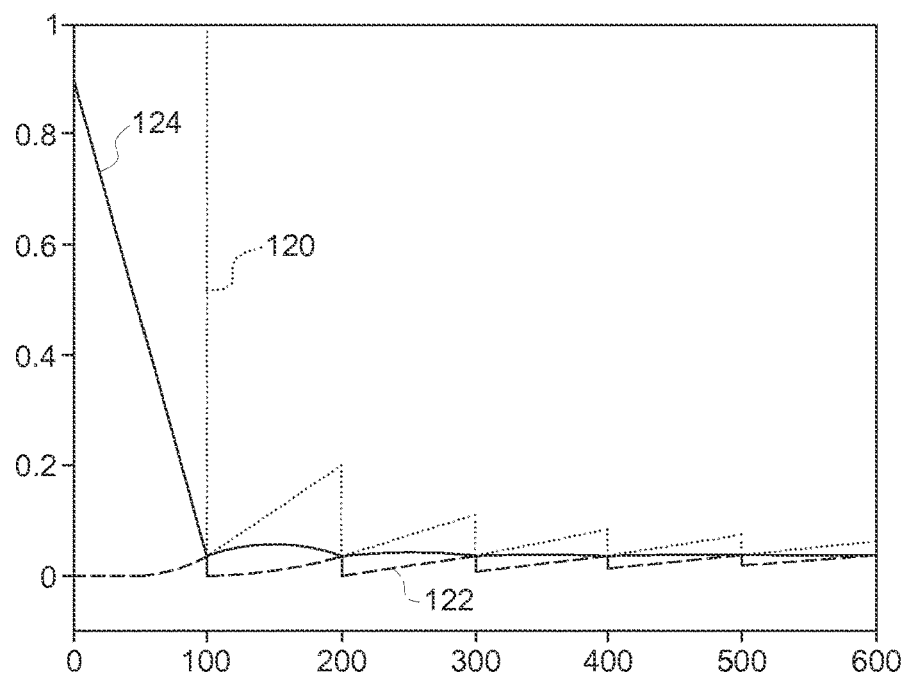
FIG. 5 graphically depicts simulated X-ray intensity attributable to an X-ray filter assembly in accordance with aspects of the present disclosure.

This result is graphically depicted in FIGS. 4 and 5. In particular, in FIG. 4, the x-axis corresponds to the fan angle region in arbitrary units, with 0 to 100 corresponding to the lowest fan angle range for X-ray in this example, while the y-axis depicts attenuation at the respective fan angles. X-rays in this fan angle range intersect zero or one attenuating sheets 80. In this example, at fan angle 0 on the x-axis, 10% of the X-rays intersect an attenuating sheet 80, while 90% do not intersect an attenuating sheet 80 (i.e., zero attenuating sheets). Since the X-rays are traveling substantially parallel to the attenuating sheets 80 at this fan angle, the path length through those attenuating sheets that are struck is very high, and the attenuation of this 10% of striking X-rays at fan angle 0 is thus correspondingly high, giving a net transmission of approximately 90% (i.e., the percent of X-rays not impacting the attenuating sheets 80 at fan angle 0). The attenuation (shown on the y-axis) may therefore be given as the negative log of 0.9 (i.e., 0.1054). As the fan angles increase, proceeding to the right along the x-axis, the average path length through impacted attenuating sheets 80 for those X-rays impacting these sheets 80 (i.e., the average intersection path length) decreases, which correspondingly decreases the attenuation for these X-rays. However, correspondingly, at increasing fan angles (moving right along the x-axis), the fraction of X-rays moving on paths that intersect an attenuating sheet 80 grows in a generally linear manner as the fan angle increases. As fan angle increases, this second observation has a larger impact (as more attenuating sheets are traversed at increased fan angles), resulting in increased overall attenuation as fan angle increases, such as from 0 to 100.

At a fan angle of 100, all X-rays interact with one attenuating sheet 80. Within the fan angle range between 100 and 200, the X-rays interact with (i.e., impact or intersect) between one and two attenuating sheets 80. Consequently, within this fan angle range, FIG. 4 depicts the plotted attenuation that corresponds to one intersection (line 120) and two intersections (line 122) respectively, as opposed to zero intersections (line 120) and one intersection (line 122) within the range of 0 to 100. That is, in FIG. 4, within each defined fan angle range, line 120 corresponds to the minimum number of intersections, line 122 corresponds to the maximum number of intersections within that range, and line 124 corresponds to the mean attenuation observed at the respective fan angle range. Thus, within the fan angle range of from 200 to 300, the attenuation is plotted that corresponds to two intersections (line 120) and three intersections (line 122) since X-rays within this range will intersect with either two or three attenuating sheets 80. The fan angle range from 100 to 200 (and subsequent higher ranges) is different from the fan angle range 0 to 100 in that the two effects mentioned above (i.e., intersection path length versus the number of intersected attenuating sheets) balance each other out somewhat from 100 to 200, with the dominant effect being the reduction of attenuation in the early part of the range, before plot 124 reaches a local minimum and the dominant effect becomes the increase in the fraction of rays that have two intersections rather than one (in the fan angle range from 100 to 200) through the portion of the fan angle range above this local minimum.

Figure 6:
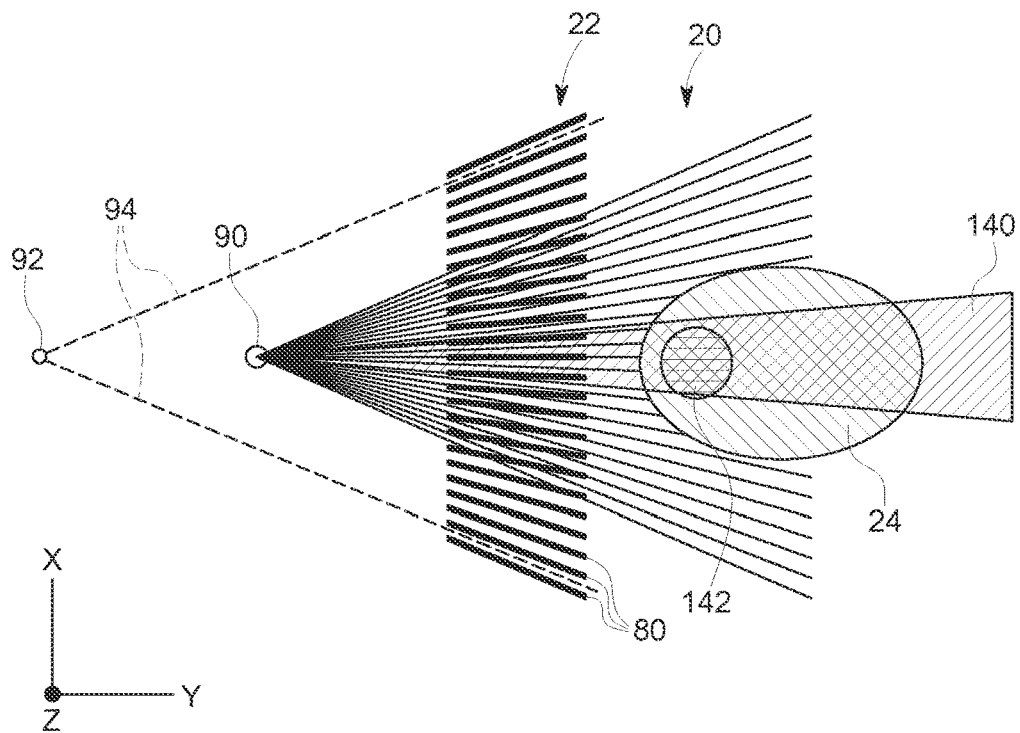
FIG. 6 depicts a schematic view of an X-ray filter assembly being used to generate a high-transmission X-ray beam focused on a region-of-interest, in accordance with aspects of the present disclosure.

Turning to FIG. 6, this figure corresponds to FIG. 5 except instead of attenuation being plotted on the y-axis, intensity is instead plotted on the y-axis. In this example, intensity is computed by skipping the negative log step used to derive attenuation described above. As with FIG. 5, within each defined fan angle range, line 120 corresponds to the minimum number of intersections, line 122 corresponds to the maximum number of intersections within that range, and line 124 corresponds to the mean attenuation observed at the respective fan angle range.

With the preceding X-ray filter discussion and examples in mind, the following figures and discussion relate various approaches that illustrate how such a filter assembly 22 may be used in an imaging context. By way of example, the filtration examples described generally relate to a region-of-interest (ROI) imaging context, where it may be desirable to focus a high intensity X-ray beam onto a limited portion of a patient's anatomy while limiting the exposure of the remainder of the patient to inadvertent X-ray dose. As will be appreciated, such a task may be difficult in certain imaging modalities, such as computed tomography (CT), tomosynthesis, or interventional/navigational contexts where one or both of the patient and/or the imaging scanner may be moved throughout the examination process. For example, in a CT context, the X-ray source 12 may be rotated rapidly about the patient (e.g., two to three rotations a second), making it difficult to focus a narrow X-ray beam on a limited portion of anatomy throughout the examination.

The present X-ray filter assembly 22 addresses several of these difficulties, allowing generation of a focused X-ray beam using a compact filter assembly that requires minimal motion to achieve the desired filtration and aiming of the X-ray beam. In particular, the present filter assembly 22 magnifies small motions (rotational and/or translational) into relatively large changes (in size or location) of the transmission spot relative to the patient.

With this in mind, FIG. 6 depicts a schematic configuration of an X-ray filter assembly 22 as discussed herein having a focus 92 spatially offset from the X-ray emission point 90. In the depicted example, the y-dimension corresponds to the direction of propagation of the X-rays at fan angle zero, the x-dimension corresponds to the fan angle direction, and the z-dimension corresponds to the scanner axis direction (i.e., the axial direction of the borehole in which the patient is positioned).

In the schematic view of FIG. 6, a high-intensity (i.e., high-transmission) portion 140 of X-ray beam 20 (such as the portion of the X-ray beam striking zero or one attenuating sheets 80) is generated while the remainder of the X-ray beam 20 is at a reduced intensity due to attenuation by the sheets 80. In the depicted example, the high-intensity beam 140 is sized and/or shaped to correspond to a region-of-interest 142 within the patient 24, so that the remainder of the patient 24 not within the path of high-intensity portion 140 receives less radiation dose.

Figure 7A:
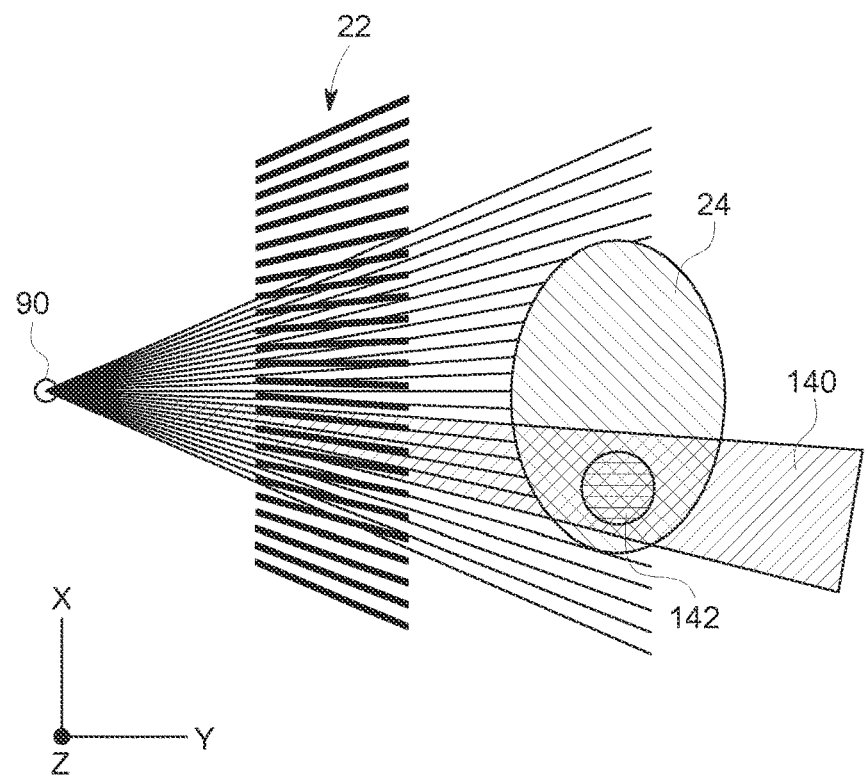
FIGS. 7A, 7B, 7C depict translation of an X-ray filter assembly in the x-dimension to steer a high-intensity X-ray beam, in accordance with aspects of the present disclosure.
Figure 7B:
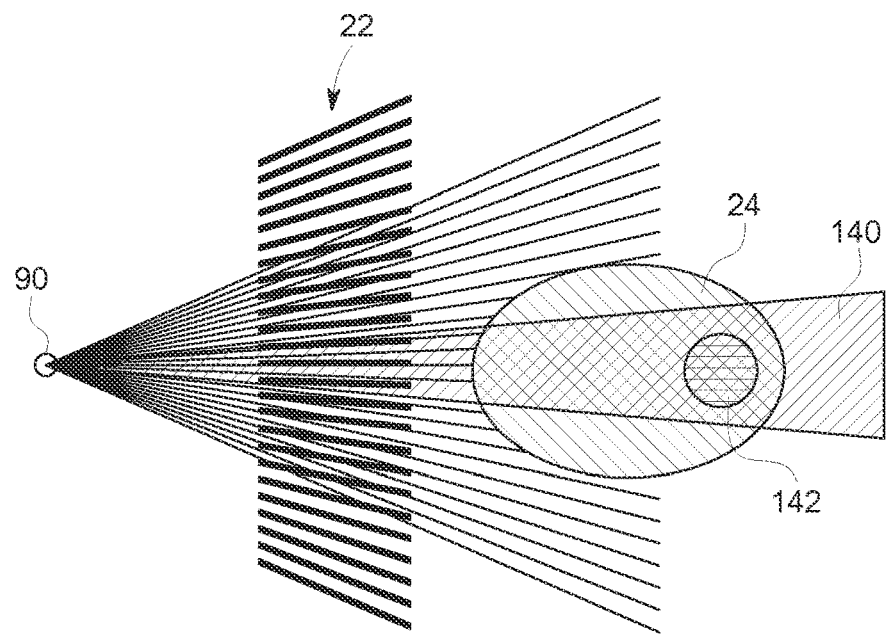
Figure 7C:
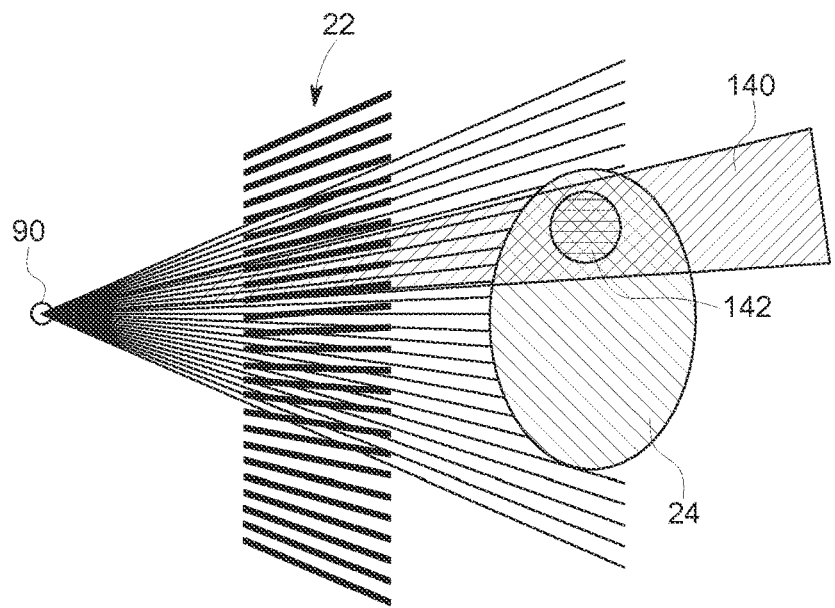

With the configuration of FIG. 6 in mind, FIGS. 7A, 7B, and 7C depict the translation of the filter assembly 22 in the x-dimension so as to steer the high-intensity portion 140 of the beam 20 during an examination. In this manner, the high-intensity portion 140 of the X-ray beam may remain directed on the region-of-interest 142 during a patient scan. It should be appreciated that, in FIGS. 7A-7C, the scanner components (e.g., X-ray emission point 90 and filter assembly 22) are presented in a generally constant orientation so as to better convey the movement (i.e., translation in the x-dimension) of the filter assembly 22 with respect to the emission point 90. Thus, the patient 24 appears to rotate with respect to the scanner components. In practice, however, the scan components will typically be rotated relative to the patient 24. In the manner shown in FIGS. 7A-7C, relatively small motions of the filter assembly 22 result in the high-intensity portion 140 of the X-ray beam remaining directed toward the region-of-interest 142 while the emission point 90 and filter assembly 22 rotate about the patient 24. In the depicted example, motion of the filter assembly 22 in the x-dimension changes the direction of the high-intensity beam portion 140, without changing the incident size of this portion 140 of the beam as observed at the region-of-interest 142.

Figure 8A:
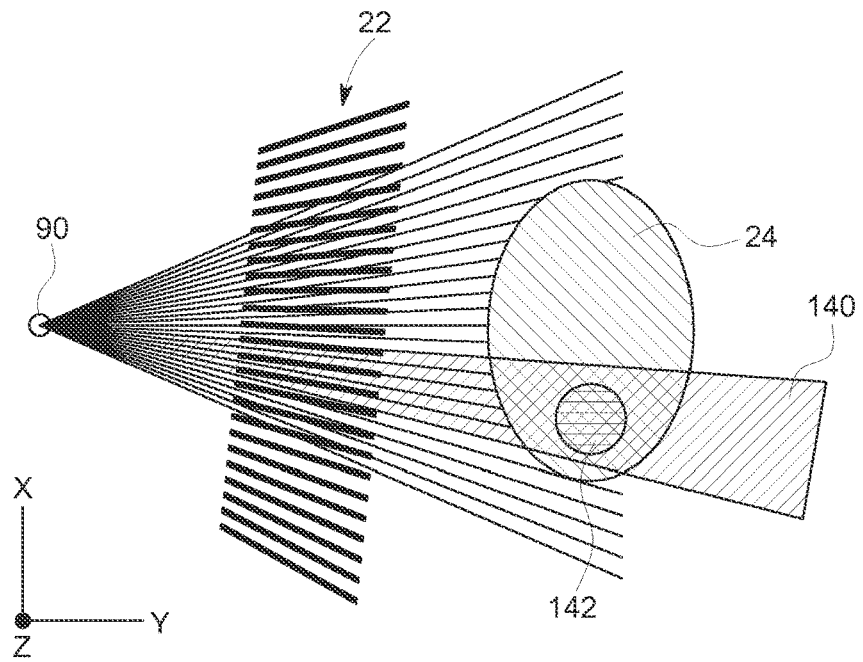
FIGS. 8A, 8B, 8C depict rotation of an X-ray filter assembly in the x,y-plane to steer a high-intensity X-ray beam, in accordance with aspects of the present disclosure.
Figure 8B:
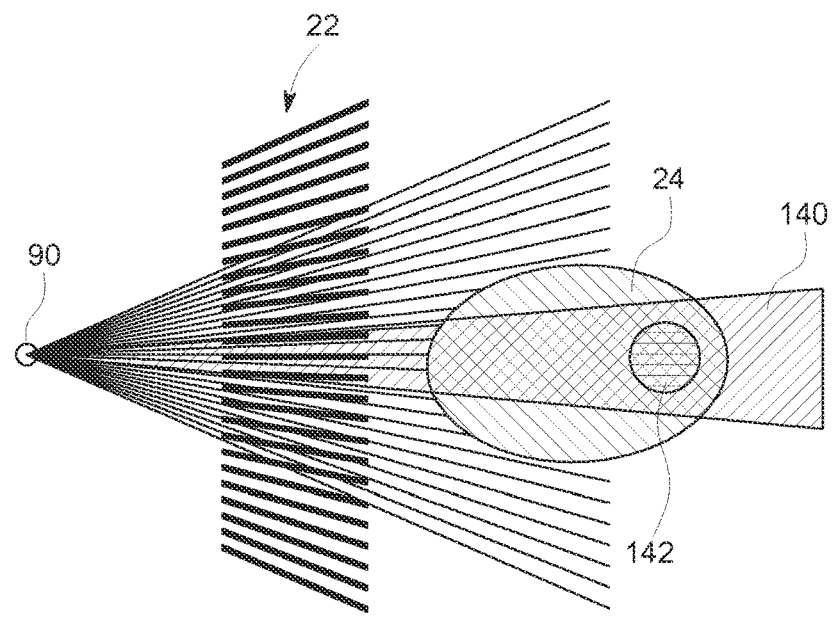
Figure 8C:
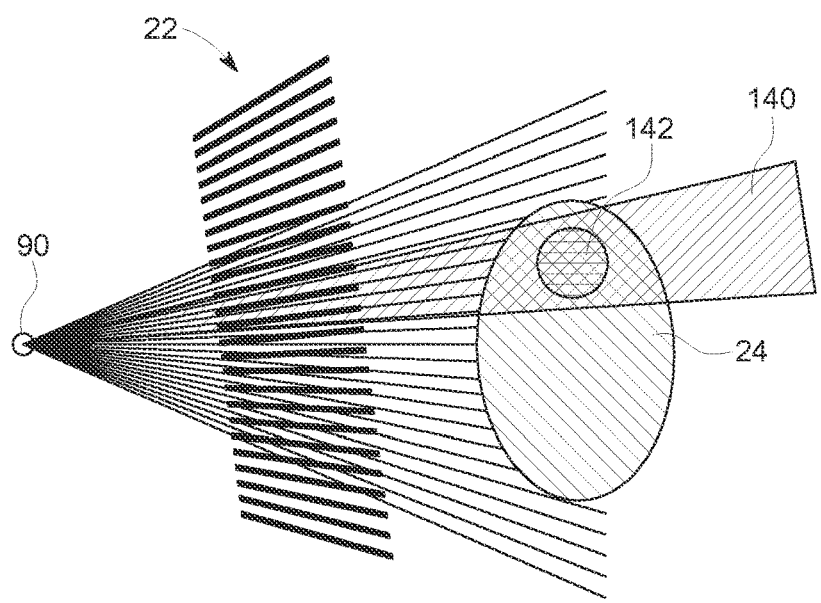
Figure 9A:
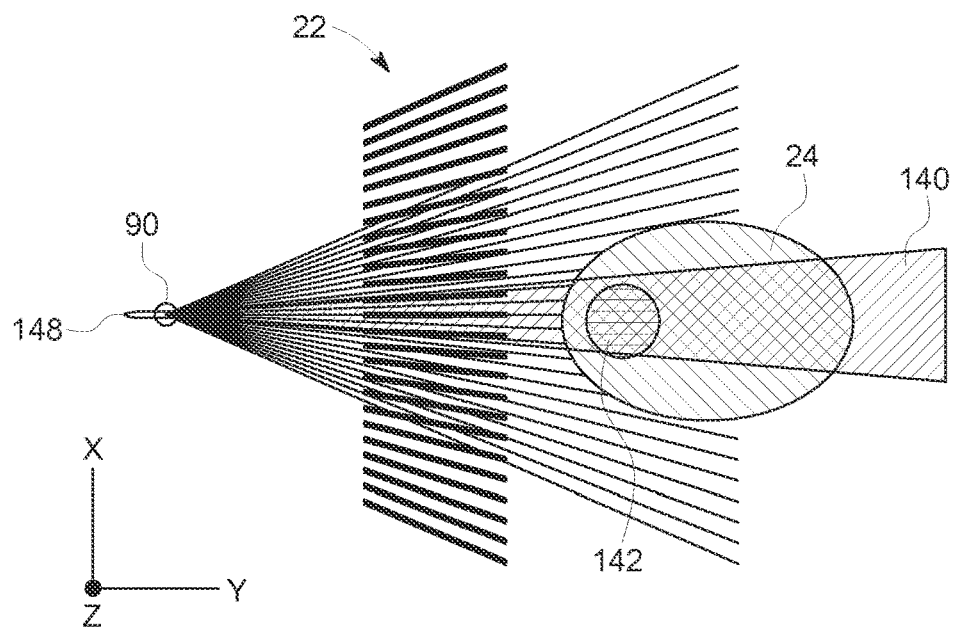
FIGS. 9A, 9B, 9C, 9D depict the use of X-ray focal spot "wobble" to steer a high-intensity X-ray beam, in accordance with aspects of the present disclosure.
Figure 9B:
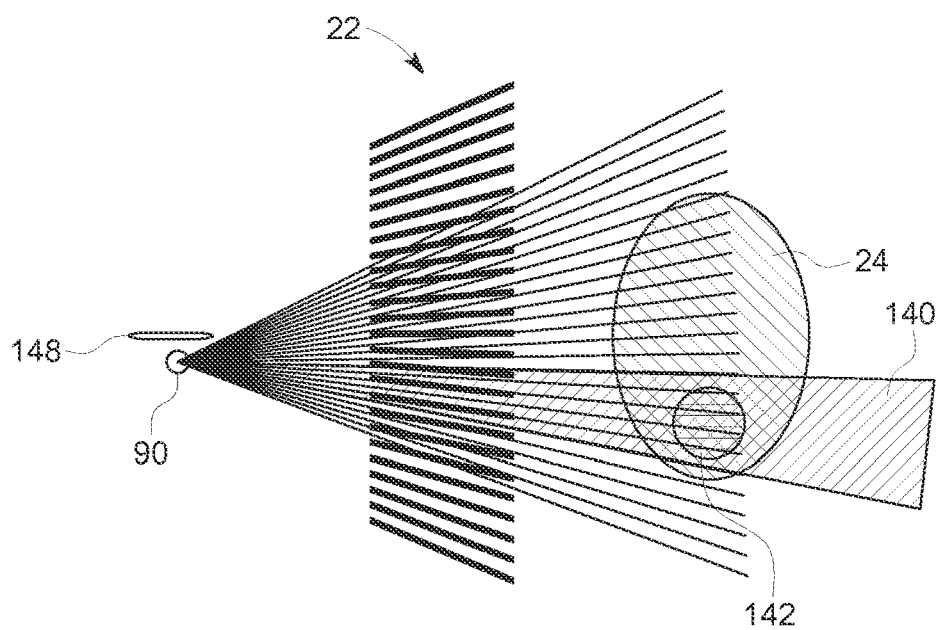
Figure 9C:
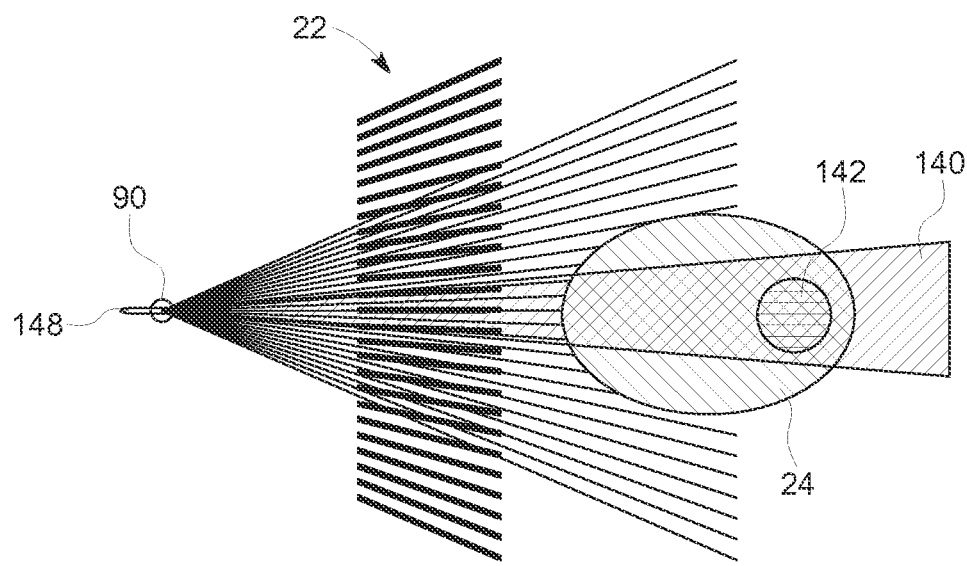
Figure 9D:
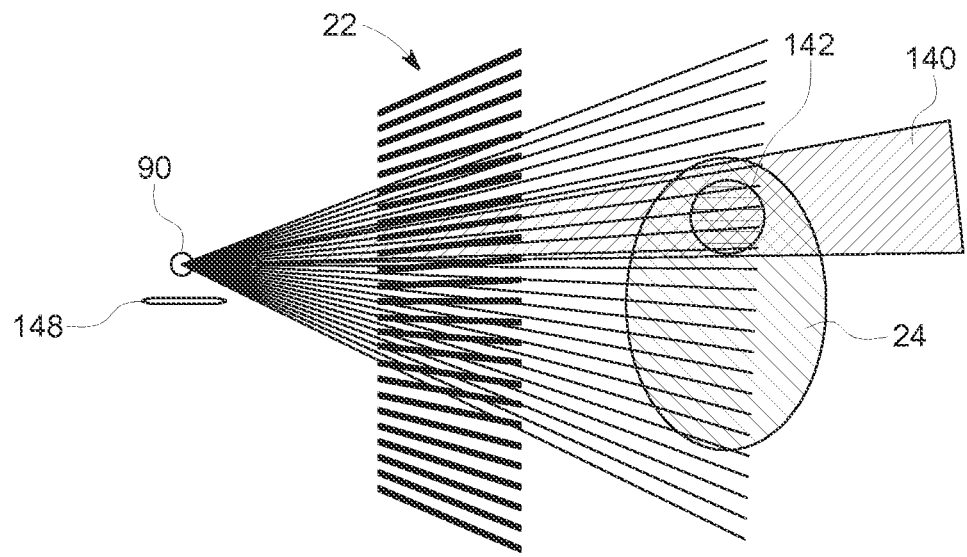

Similarly, FIGS. 8A, 8B, and 8C depict the rotational movement of the filter assembly 22 within the x,y-plane as a technique for steering the high-intensity portion 140 of the beam 20 during an examination. In this manner, the high-intensity portion 140 of the X-ray beam may remain directed on the region-of-interest 142 during a patient scan. As with the preceding example, in FIGS. 8A-8C the scanner components (e.g., X-ray emission point 90 and filter assembly 22) are presented in a generally constant orientation so as to better convey the movement (i.e., rotation in the x,y-plane) of the filter assembly 22 with respect to the emission point 90. Thus, as in the preceding example, the patient 24 appears to rotate with respect to the scanner components. In practice, however, the scan components will typically be rotated relative to the patient 24. In the manner shown in FIGS. 8A-8C, relatively small rotational motions of the filter assembly 22 result in the high-intensity portion 140 of the X-ray beam remaining directed toward the region-of-interest 142 while the emission point 90 and filter assembly 22 are moved about the patient 24. In this example, rotational motion of the filter assembly 22 in the x,y-plane changes the direction of the high-intensity beam portion 124, without changing the incident size of this portion 140 of the beam as observed at the region-of-interest 142.

An alternative approach is shown with respect to FIGS. 9A, 9B, 9C, and 9D. In particular, in this example, the filter assembly 22 is not moved (either translated or rotated) and instead the focal spot 90 associated with X-ray emission is "wobbled" (e.g., alternated or sequentially moved) between different emission locations relative to a central reference 148 on a source target. The emission locations may be different discrete locations that are sequentially targeted by an electron beam used to generate the X-rays or may be a continuous surface (linear or otherwise) on which the electron-beam is moved during imaging so as to elicit X-ray generation along the continuous surface on the target.

In this manner, movement of the X-ray emission point 90 achieves a result similar to what is seen when the filter assembly 22 is moved in the x-dimension, but without the mechanical motion of the filter assembly. As shown in this example, the high-intensity portion 140 of the X-ray beam may remain directed on the region-of-interest 142 during a patient scan. In particular, and as shown in FIGS. 9A-9D, the movement of the emission point 90 relative to the filter assembly 22 results in the high-intensity portion 140 of the X-ray beam remaining directed toward the region-of-interest 142 while the emission point 90 and filter assembly 22 rotate about the patient 24. In the depicted example, the "wobble" introduced in the emission point 90 location allows redirection of the high-intensity beam portion 140, without changing the incident size of this portion 140 of the beam as observed at the region-of-interest 142.

The preceding examples demonstrate techniques by which the filter assembly 22 may be steered or directed so as to remain directed toward a region-of-interest while maintaining generally the same size (i.e., field-of-view) at the region of interest. The following example, conversely, shows how the filter assembly 22 may be moved (i.e., translated) so as to change the size of the field of view (i.e., the size or width of the high-intensity portion 140), as opposed to the beam direction, with respect to the patient. Such an approach may allow a user to limit high-intensity X-ray exposure of the patient 24 outside the region-of-interest 142, while still providing good image quality within the region-of-interest. It should be noted that, unlike the preceding examples, the present example is shown in the context of a stationary patient 24 and scanner (i.e., without rotation about the patient 24), though it should be appreciated that the present approach can be implemented in conjunction with relative motion (rotational or otherwise) with respect to the patient 24 and scanner.

Figure 10A:
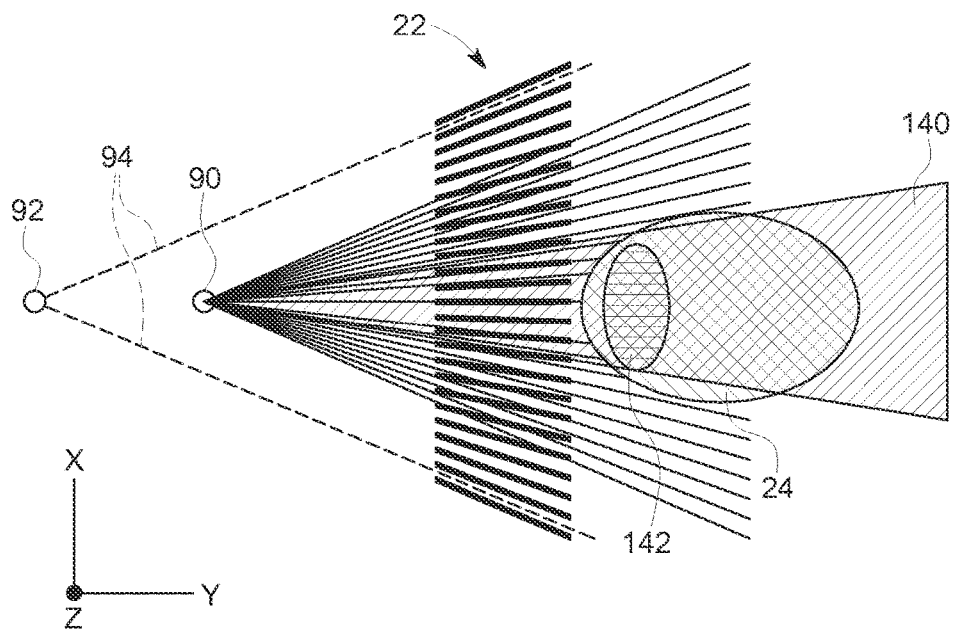
FIGS. 10A, 10B, 10C depict translation of an X-ray filter assembly in the y-dimension to adjust the size of a high-intensity X-ray beam, in accordance with aspects of the present disclosure.
Figure 10B:
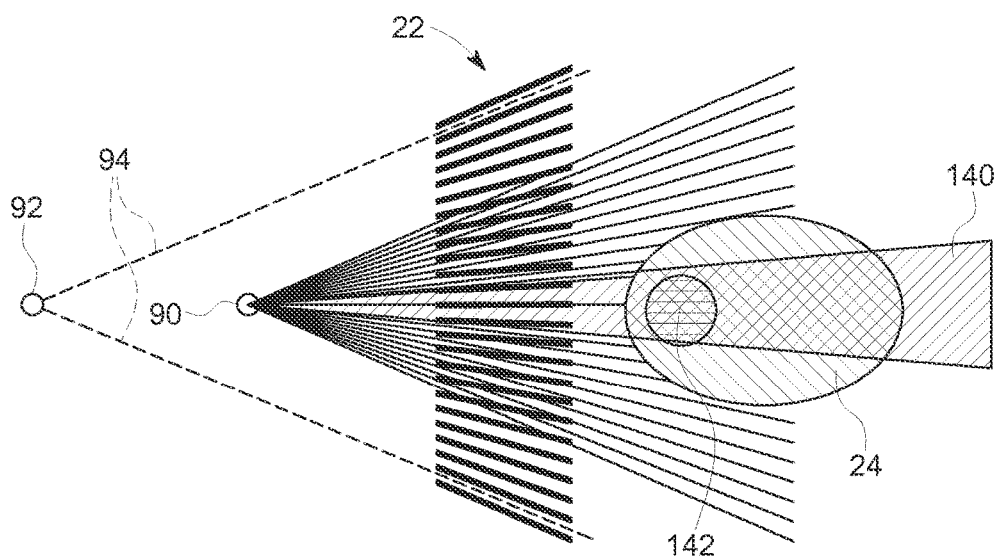
Figure 10C:
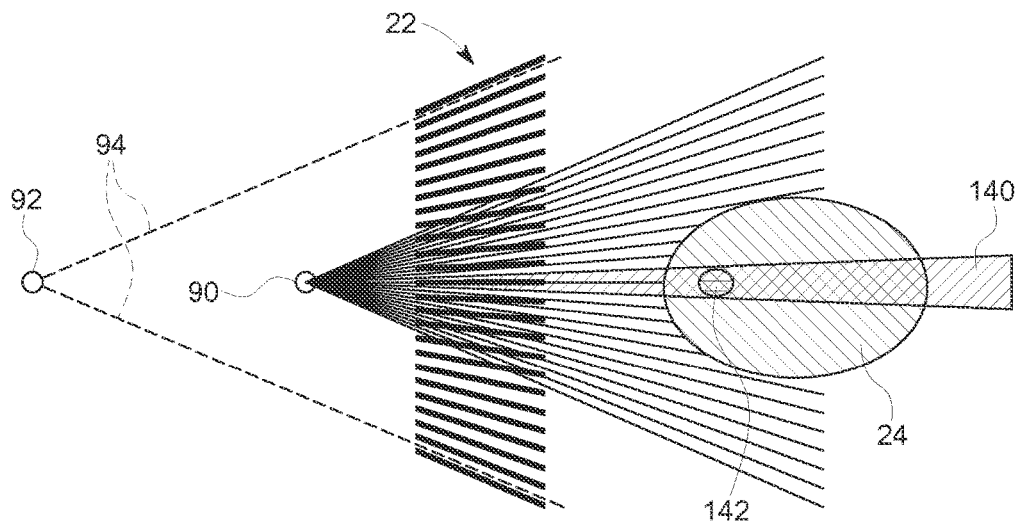

With this in mind, FIGS. 10A, 10B, and 10C depict an example in which the filter assembly 22 is translated in the y-dimension, effectively moving the filter assembly 22 closer to, or further from, the X-ray emission point 90. Due to the offset focus of the filter assembly 22, motion in this dimension varies the diameter or width (i.e., the aperture) of the high-intensity portion 140 of the X-ray beam observed at the patient. In this manner, a user may vary the size of the field-of-view associated with the beam portion 140, allowing the diameter or width of the beam to be sized to correspond to the size of the region-of-interest 142. Correspondingly, the X-ray exposure of portions of the patient 24 outside the region-of-interest 142 may be minimized or otherwise reduced.

A similar result may be achieved without employing motion in the y-dimension. In particular, in a further embodiment, two (or more) filtration assemblies 22 may be provided that are side-by-side or adjacent in the z-dimension. In such an embodiment, the filtration assemblies 22 may have different focus points 92 (e.g., focus points 92 that are differently offset from the X-ray emission point 90). In such an arrangement, the system may switch between the different filtration assemblies 22, such as by moving the filter assemblies 22 in the z-dimension to select which assembly 22 is in the X-path 20 at a given time. Due to the different focus points 90 of the respective assemblies, each filter will have a different effective width or diameter of the high-intensity portion 140 that is passed through to the patient.

Figure 11:
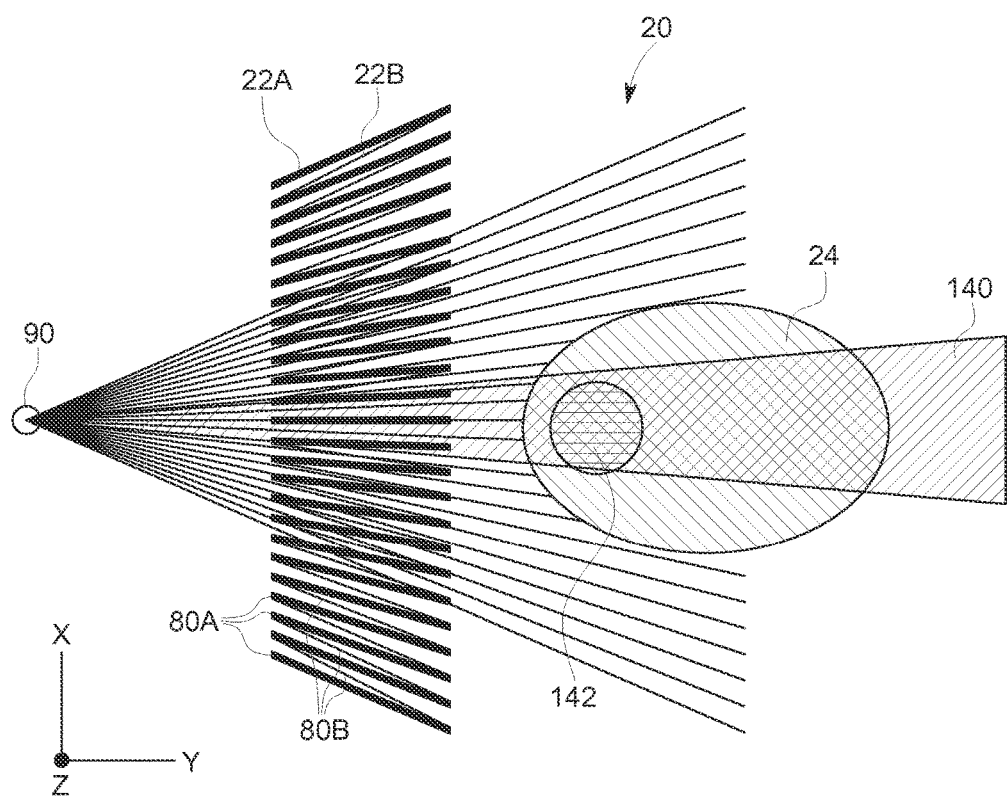
FIG. 11 depicts the use of multiple X-ray filtration assemblies, in accordance with aspects of the present disclosure.

An example of one such arrangement is shown in FIG. 11, where two filter assemblies 22A and 22B are shown side-by-side in the z-dimension, with assembly 22A being closer to the viewer in the depicted arrangement. In the depicted example, filtration assemblies 22A and 22B can be seen to be composed of attenuating sheets 80A and 80B respectively that are differently angled with respect to one another, giving rise to different focus points for the different filtration assemblies. Thus, moving the adjacent assemblies in the z-dimension may effectively substitute one assembly for the other in the X-ray path, and may thereby change the size of the X-ray spot seen at the patient via this motion in the z-dimension, without motion in the y-dimension.

Note that the preceding examples have been explained separately for the sake of simplicity and generally facilitate explanation and understanding of the use of an X-ray filter assembly, as discussed herein. It should be appreciated that some or all of the above approaches (e.g., translation in the x-dimension, rotation in the x,y-plane, translation in the y-dimension, focal spot wobble, and/or use of multiple assemblies that may be switched between) may be used in combination to achieve the desired filtration effects. For example, certain of the above-techniques may be used in combination to allow both beam-steering and dynamic adjustment of the X-ray spot size observed at the patient.

Technical effects of the disclosed embodiments include an X-ray filter assembly having a stack of X-ray attenuating sheets that are angled so as to have a focus point. When implemented in an imaging system, the focus point of the filter assembly is spatially offset (e.g., behind) the X-ray emission location. The present filter assembly may be used (e.g., translated, rotated, and so forth) to adjust the intensity profile of the X-rays seen in the imaging volume (e.g., patient). In certain embodiments, use of the presently disclosed X-ray filter assembly allows small motion of the filter assembly to result in relatively large motion of the X-ray spot or relatively large changes in size of the X-ray spot.

This written description uses examples to disclose the subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray filter assembly, comprising:
a plurality of X-ray attenuating sheets arranged in a stack, wherein the X-ray attenuating sheets are angled with respect to one another so as to have a focus point that is converged upon by transmission pathways between the X-ray attenuating sheets; and a plurality of X-ray transmissive sheets disposed alternately with the plurality of X-ray attenuating sheets such that a respective X-ray transmissive sheet is positioned between each adjacent pair of X-ray attenuating sheets,
wherein the X-ray transmissive sheets have a tapered profile that varies in thickness across at least part of their length so that, when stacked, the adjacent X-ray attenuating sheets are angled with respect to one another,
further wherein tapering of the transmissive sheets determine a focus point of the filter assembly when the stack is assembled and wherein a position and/or an orientation of the filter assembly relative to the focus point allow beam-steering without a mechanical motion of the filter assembly, and/or dynamic adjustment of an X-ray spot size observed at a patient.

2. The X-ray filter assembly of claim 1, wherein the X-ray transmissive sheets define the transmission pathways between the X-ray attenuating sheets.

3. The X-ray filter assembly of claim 1, wherein the X-ray transmissive sheets are formed from at least a polyimide film.

4. The X-ray filter assembly of claim 1, wherein each X-ray transmissive sheet has a thickness of approximately 1 to 50 mils.

5. The X-ray filter assembly of claim 1, wherein the X-ray attenuating sheets are formed from one or more of molybdenum, tungsten, iron, nickel, zinc, copper, silver, tin, tantalum, gold, lead, or rhenium film.

6. The X-ray filter assembly of claim 1, wherein each X-ray attenuating sheet has a thickness of approximately 0.1 to 5 mils.

7. The X-ray filter assembly of claim 1, further comprising a mounting assembly configured to hold the stack of X-ray attenuating sheets in alignment.

8. The X-ray filter assembly of claim 7, wherein the mounting assembly is configured to be positioned with a gantry of a computed tomography (CT) imager between an X-ray source and an imaged volume.

9. An X-ray imaging system, comprising:
an X-ray detector configured to generate signals in response to incident X-ray radiation;
an X-ray source configured to emit X-rays from an X-ray emission point and through an imaging volume toward the X-ray detector;
a data acquisition system configured to readout signals from the X-ray detector; and at least one X-ray filter positioned between the X-ray source and the imaging volume;

wherein the X-ray filter or filters have a focus point that is spatially offset from the X-ray emission point, and further wherein the X-ray filter or filters each comprise a stack of alternating X-ray attenuating sheets and X-ray transmissive sheets, wherein the X-ray transmissive sheets have a tapered profile that varies in thickness across at least part of their length so that, the adjacent X-ray attenuating sheets are angled with respect to one another, further wherein tapering of the transmissive sheets determine a focus point of the filter assembly when the stack is assembled and wherein a position and/or an orientation of the filter assembly relative to the focus point allow beam-steering without a mechanical motion of the filter assembly, and/or dynamic adjustment of an X-ray spot size observed at a patient.

10. The X-ray imaging system of claim 9, wherein the X-ray filter or filters have a focus point that is behind the X-ray emission point with respect to the X-ray source and respective X-ray filter.

11. The X-ray imaging system of claim 9, wherein the X-ray filter or filters are mounted proximate to a window of the X-ray source.

12. The X-ray imaging system of claim 9, wherein the X-ray filter or filters are configured to be one or both of translated or rotated with respect to the X-ray emission point.

13. The X-ray imaging system of claim 9, wherein the X-ray filter or filters are configured to remain stationary while the X-ray emission points are moved.

14. A method for filtering X-rays, comprising:

generating X-rays at an X-ray emission point of an X-ray source;

filtering at least a portion of the X-rays through an X-ray filter assembly positioned between the X-ray source and an imaging volume;

disposing a plurality of X-ray transmissive sheets alternately with the plurality of X-ray attenuating sheets such that a respective X-ray transmissive sheet is positioned between each adjacent pair of X-ray attenuating sheets, wherein the X-ray transmissive sheets have a tapered profile that varies in thickness across at least part of their length so that, when stacked, the adjacent X-ray attenuating sheets are angled with respect to one another and further wherein the X-ray transmissive sheets define a plurality of transmission pathways between the X-ray attenuating sheets;

determining a focus point corresponding to a convergence point of the plurality of transmission pathways between the attenuating sheets, wherein the focus point is spatially offset from the X-ray emission point;

positioning and/or an orientating the filter assembly relative to the focus point to steer an X-Ray beam without mechanically moving the filter assembly, and/or dynamically adjusting an X-ray spot size observed at a patient; and detecting X-rays at a detector positioned opposite the X-ray source and X-ray filter assembly across the imaging volume.

15. The method of claim 14, wherein filtering the X-rays comprises moving the X-ray filter assembly in one or both of a first direction corresponding to a fan angle direction or a second direction corresponding to a direction of propagation of the X-rays at fan angle zero.

16. The method of claim 14, wherein filtering the X-rays comprises rotating the X-ray filter assembly.

17. The method of claim 14, wherein filtering the X-rays comprises moving the X-ray emission point with respect to the X-ray filter assembly.

* * * * *